(12) United States Patent
Park et al.

(10) Patent No.: US 7,716,169 B2
(45) Date of Patent: May 11, 2010

(54) SYSTEM FOR AND METHOD OF EXTRACTING AND CLUSTERING INFORMATION

(75) Inventors: Sung Hee Park, Daejeon (KR); Dae Hee Kim, Daejeon (KR); Chan Yong Park, Daejeon (KR); Seon Hee Park, Daejeon (KR)

(73) Assignee: Electronics and Telecommunications Research Institute, Dajeon (KR)

( * ) Notice: Subject to any disclaimer, the term of this patent is extended or adjusted under 35 U.S.C. 154(b) by 153 days.

(21) Appl. No.: 11/635,447

(22) Filed: Dec. 7, 2006

(65) Prior Publication Data

US 2007/0136277 A1      Jun. 14, 2007

(30) Foreign Application Priority Data

Dec. 8, 2005    (KR) .................. 10-2005-0119469
Nov. 15, 2006   (KR) .................. 10-2006-0113050

(51) Int. Cl.
*G06F 7/00*    (2006.01)

(52) U.S. Cl. .................. 707/103 Z; 707/101; 707/102; 707/104.1

(58) Field of Classification Search .................. 707/10, 707/102, 103 R, 6, 4, 100, 103 Z, 101, 104.1; 706/21, 30; 715/500
See application file for complete search history.

(56) References Cited

U.S. PATENT DOCUMENTS

| 6,226,408 B1 * | 5/2001 | Sirosh ................ 382/224 |
|---|---|---|
| 6,374,251 B1 | 4/2002 | Fayyad et al. |
| 7,092,941 B1 * | 8/2006 | Campos ................ 707/6 |
| 7,143,045 B2 * | 11/2006 | Sekiguchi ................ 704/275 |
| 2002/0019826 A1 | 2/2002 | Tan |
| 2004/0078386 A1 * | 4/2004 | Moon et al. ................ 707/102 |
| 2004/0098412 A1 | 5/2004 | Raspl |
| 2004/0249809 A1 * | 12/2004 | Ramani et al. ................ 707/4 |
| 2005/0097436 A1 * | 5/2005 | Kawatani ................ 715/500 |
| 2005/0256851 A1 * | 11/2005 | Nakamura et al. ................ 707/3 |
| 2006/0004751 A1 * | 1/2006 | Ujino et al. ................ 707/6 |
| 2006/0184475 A1 * | 8/2006 | Krishnan et al. ................ 706/20 |
| 2007/0033218 A1 * | 2/2007 | Taylor ................ 707/102 |
| 2007/0112704 A1 * | 5/2007 | Tomkins et al. ................ 706/21 |
| 2007/0162473 A1 * | 7/2007 | Hadzikadic et al. ................ 707/100 |

FOREIGN PATENT DOCUMENTS

EP         1460559        9/2004

(Continued)

OTHER PUBLICATIONS

Daniela Rus et al., "Customizing Information Capture and Access", ACM, Jan. 1997, pp. 67-101.*

(Continued)

*Primary Examiner*—Thuy N Pardo
(74) *Attorney, Agent, or Firm*—Blakely, Sokoloff, Taylor & Zafman LLP

(57) ABSTRACT

Provided is a system for and method of extracting and clustering information. The system includes a clustering criterion designing unit that reconstructs a plurality of clustering criteria for each layer or applies weights to the plurality of clustering criteria in order to design a new clustering criterion, an input data processing unit that extracts characteristics from input data according to the new clustering criterion, and a clustering unit that performs clustering on the extracted characteristics.

11 Claims, 4 Drawing Sheets

FOREIGN PATENT DOCUMENTS

| | | |
|---|---|---|
| JP | 2001-175660 A | 6/2001 |
| JP | 2003-344270 A | 12/2003 |
| JP | 2005-078245 A | 3/2005 |
| KR | 2001-0064269 | 7/2001 |
| KR | 2003-0019682 | 3/2003 |
| WO | WO-02/11048 | 2/2002 |
| WO | WO-03/054770 | 7/2003 |
| WO | WO 2005/036441 A1 | 4/2005 |
| WO | WO 2005/050479 A1 | 6/2005 |

OTHER PUBLICATIONS

A. K. Jain et al., "Data clustering: A review", ACM, Sep. 1999, pp. 264-323.*

Elias Pampalk et al, "Content-based organization and visualization of music archieves", ACM, 2002, pp. 570-579.*

Sun, Y. et al. "An iterative initial-points refinement algorithm for categorical data clustering"; *Pattern Recognition Letters 23*; vol. 23; pp. 875-884; Amsterdam, NL, May 2002.

Kolasakar, A.S. et al. "Prediction of conformational states of amino acids using a Ramachandran plot"; *International Journal of Peptide & Protein Research*; vol. 47; pp. 110-116; Belgium, Aug. 28, 1995.

Park, Sung Hee, et al., "Automatic Protein Structure Clustering Using Secondary Structure Elements," RECOMB2005, The Ninth Annual International Conference on Research in Computational Molecular Biology, Cambridge, MA (May 14-18, 2005) pp. 247-248.

* cited by examiner

FIG. 3

| FIELD | ATOM NO. | ATOM NAME | AMINO ACID NAME | CHAIN | AMINO ACID SEQUENCE | ATOM 3D COORDINATES | | | | | ATOM SYMBOL |
|---|---|---|---|---|---|---|---|---|---|---|---|
| ATOM | 1 | N | GLU | A | 534 | 23.444 | 69.516 | 71.429 | 1.00 | 30.81 | N |
| ATOM | 2 | CA | GLU | A | 534 | 24.464 | 68.436 | 71.442 | 1.00 | 30.75 | C |
| ATOM | 3 | C | GLU | A | 534 | 23.839 | 67.140 | 71.905 | 1.00 | 31.03 | C |
| ATOM | 4 | O | GLU | A | 534 | 23.203 | 67.095 | 72.960 | 1.00 | 31.75 | O |
| ATOM | 5 | CB | GLU | A | 534 | 25.628 | 68.784 | 72.365 | 1.00 | 30.47 | C |
| ATOM | 6 | CG | GLU | A | 534 | 26.608 | 67.770 | 71.172 | 1.00 | 30.65 | C |
| ATOM | 7 | CD | GLU | A | 534 | 27.608 | 67.770 | 71.172 | 1.00 | 30.55 | C |

SYSTEM FOR AND METHOD OF EXTRACTING AND CLUSTERING INFORMATION

CROSS-REFERENCE TO RELATED PATENT APPLICATION

This application claims the benefit of Korean Patent Application No. 10-2005-0119469, filed on Dec. 8, 2005 and Korean Patent Application No. 10-2006-0113050, filed on 15 Nov. 2006, in the Korean Intellectual Property Office, the disclosure of which is incorporated herein in its entirety by reference.

BACKGROUND OF THE INVENTION

1. Field of the Invention

The present invention relates to a system for and method of extracting useful information from input data and clustering the extracted information, and more particularly, to a system for and method of extracting and clustering information, in which clustering can be performed according to a criterion desired by a user.

2. Description of the Related Art

Clustering is a general method for extracting desired information from a large amount of data. Clustering involves forming a cluster of information from input data in an unsupervised manner, i.e., naturally forming a group of information having similar characteristics. In general, criteria for naturally forming a cluster are predefined in a clustering system. Thus, since the clustering depends on criteria that are predefined in the clustering system, it cannot be performed according to a criterion desired by a user.

SUMMARY OF THE INVENTION

The present invention provides a system for and method of extracting and clustering information, in which previously stored clustering criteria are reconstructed according to a criterion desired by a user and useful information is extracted from input data and is then clustered according to the reconstructed criteria.

According to one aspect of the present invention, there is provided a system for extracting and clustering information. The system includes a clustering criterion designing unit that reconstructs hierarchy of a plurality of clustering criteria or applies weights to the clustering criteria in order to design a new clustering criterion, an input data processing unit that extracts characteristics from input data according to the new clustering criterion, and a clustering unit that performs clustering on the extracted characteristics.

According to another aspect of the present invention, there is provided a method of extracting and clustering information. The method includes reconstructing hierarchy of a plurality of clustering criteria or applying weights to the plurality of clustering criteria in order to design a new clustering criterion, extracting characteristics from input data according to the new clustering criterion, and performing clustering on the extracted characteristics.

Thus, various clustering operations can be performed according to criteria desired by a user.

BRIEF DESCRIPTION OF THE DRAWINGS

The above and other features and advantages of the present invention will become more apparent by describing in detail an exemplary embodiment thereof with reference to the attached drawings in which:

FIG. 3 illustrates data of a protein three-dimensional (3D) structure data base.

DETAILED DESCRIPTION OF THE INVENTION

Hereinafter, an exemplary embodiment of the present invention will be described in detail with reference to the accompanying drawings.

Figure 1:
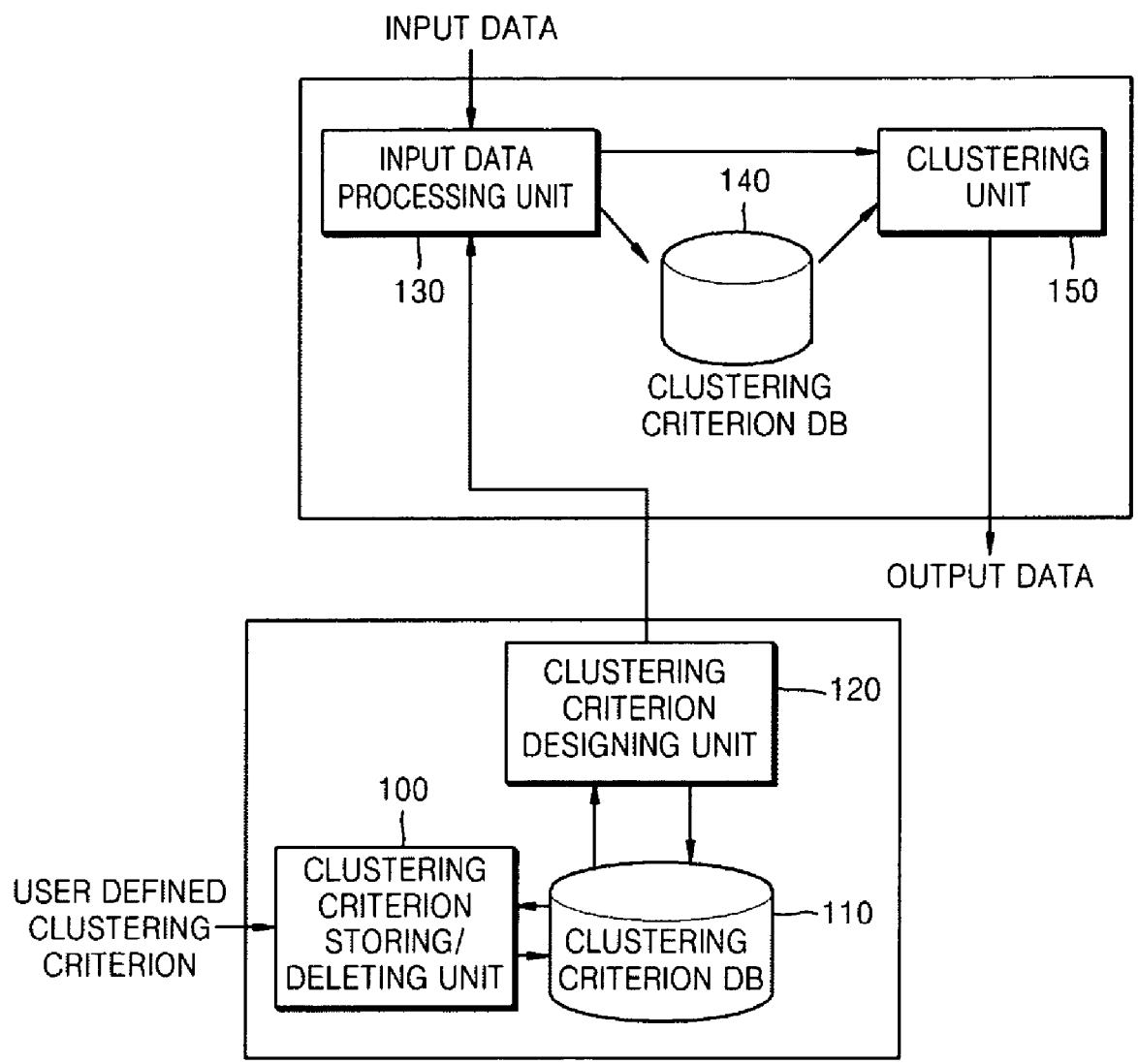
FIG. 1 is a block diagram of a system for extracting and clustering information according to an exemplary embodiment of the present invention.

FIG. 1 is a block diagram of a system for extracting and clustering information according to an exemplary embodiment of the present invention.

Referring to FIG. 1, the system includes a clustering criterion storing/deleting unit 100, a clustering criterion database 110, a clustering criterion designing unit 120, an input data processing unit 130, a clustering characteristic database 140, and a clustering unit 150.

The clustering criterion storing/deleting unit 100 receives a clustering criterion from a user and stores the received clustering criterion in the clustering criterion database 110 or deletes a clustering criterion stored in the clustering criterion database 110 at a user's request.

The clustering criterion database 110 stores a clustering criterion stored by the clustering criterion storing/deleting unit 100.

After the clustering criterion designing unit 120 requests and receives clustering criteria stored in the clustering criterion database 110, it reconstructs hierarchy of the received clustering criteria or applies weights to the received clustering criteria in order to design a new clustering criterion. In order for the clustering criterion designing unit 120 to reconstruct the clustering criteria received from the clustering criterion database 110, hierarchical criterion designing (400 and 410 of FIG. 4) and criterion designing by applying weights (420 and 430 of FIG. 4) may be used.

In criterion designing by applying weights, when clustering criteria are $C1, C2, \ldots, Cn$ and weights applied to the clustering criteria are $w1, w2, \ldots, wn$, new clustering criteria are set as $w1*C1+w2*C2+ \ldots +wn*Cn$.

The input data processing unit 130 extracts necessary characteristics according to hierarchy designed by the clustering criterion designing unit 120 or a characteristic extraction method defined in a criterion equation for applying weights and transmits the extracted characteristics to the clustering characteristic database 140.

The clustering characteristic database 140 receives the characteristics to be used for clustering from the input data processing unit 130 and stores the received characteristics. When the clustering unit 150 performs clustering on the same characteristics using different clustering methods, it uses the characteristics stored in the clustering characteristic database 140, thereby reducing the time required for the input data processing unit 130 to extract necessary characteristics.

The clustering unit 150 receives the characteristics from the clustering characteristic database 140 and performs clustering of the received characteristics. The result of clustering is output through an output device (not shown).

Figure 2:
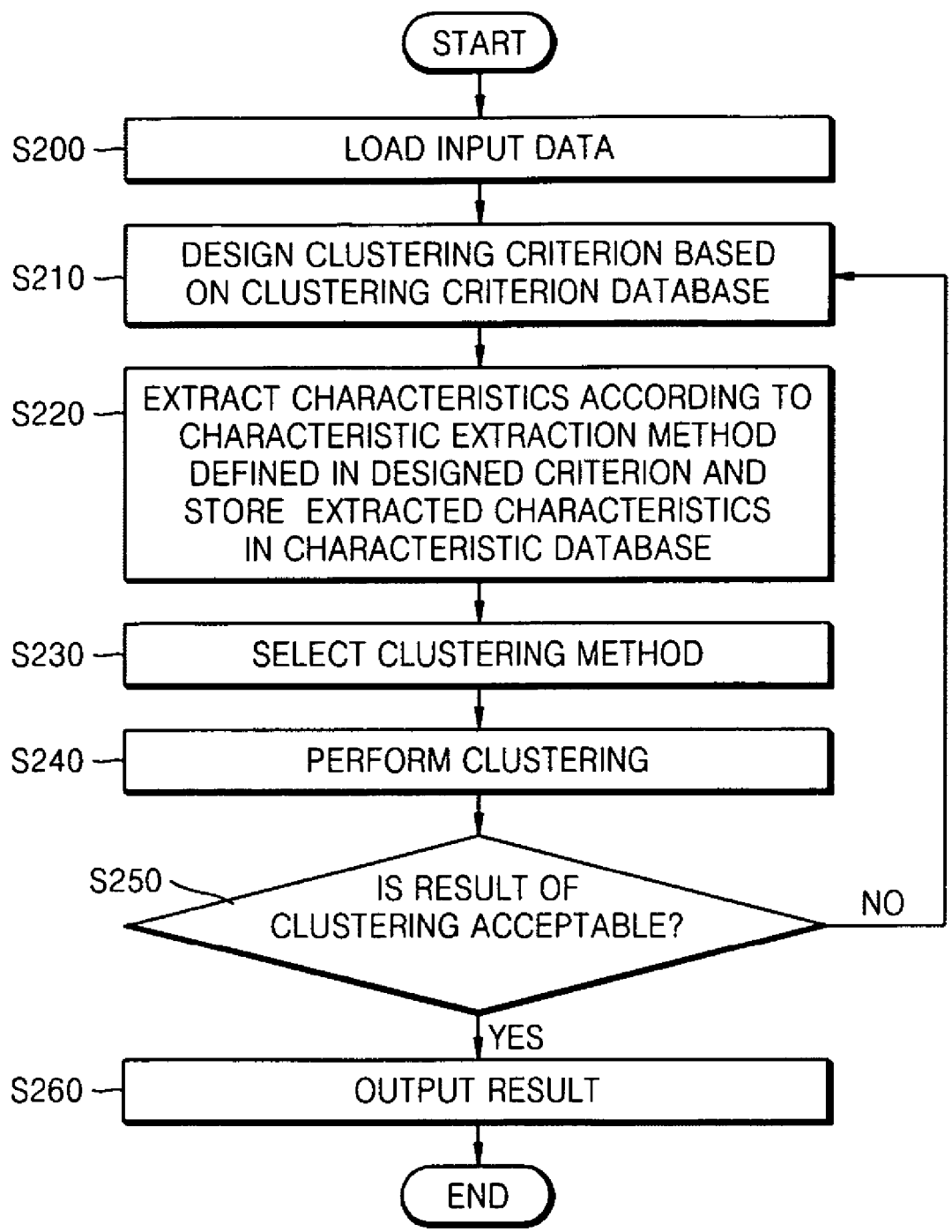
FIG. 2 is a flowchart illustrating a method of extracting and clustering information according to an exemplary embodiment of the present invention.

FIG. 2 is a flowchart illustrating a method of extracting and clustering information according to an exemplary embodiment of the present invention. In particular, in the method of FIG. 2, the system illustrated in FIG. 1 is used as a protein structure-based clustering system.

Referring to FIGS. 1 and 2, the input data processing unit 130 receives data of a protein three-dimensional (3D) structure data bank as input data in operation S200. FIG. 3 illustrates data of a protein 3D structure data bank. Referring to FIG. 3, the protein 3D structure data bank includes position information about positions of atoms of protein in the form of 3D x, y, and z coordinates.

The clustering criterion designing unit 120 reconstructs the clustering criteria stored in the clustering criterion database 110 to design a new clustering criterion in operation S210. Since the clustering criteria stored in the clustering criterion database 110 exist in the form of classes, child criterion classes inherit the criteria of parent criterion classes.

Clustering criteria used for protein structure-based clustering, which are taken as an example in the method of FIG. 2, are "number of two-dimensional (2D) structures", "distribution of the 2D structures", "sequence of the 2D structures", "protein sequence", "3D edge histogram", "regression", and "Ramachandran map".

For example, when a researcher desires to cluster data according to similar active sites to develop a new medicine, the researcher stores an "active site" clustering criterion in the clustering criterion database 110 through the clustering criterion storing/deleting unit 100. The clustering criterion designing unit 120 then reconstructs the "active site" clustering criterion with various clustering criteria that are previously stored in the clustering criterion database 110 to design a new clustering criterion.

As another example, in order to cluster data according to a characteristic protein structure, i.e., a 2D structure, and then according to protein having similar 3D structures, clustering is first performed according to the "number of 2D structures" or "distribution of the 2D structures" clustering criterion and then the result of clustering is clustered according to the "3D edge histogram" or "regression" clustering criterion, thereby obtaining a desired structural clustering result.

In hierarchical criterion designing, clustering may be performed according to the overall 3D structure of protein and then according to the number of 2D structures.

Figure 4:
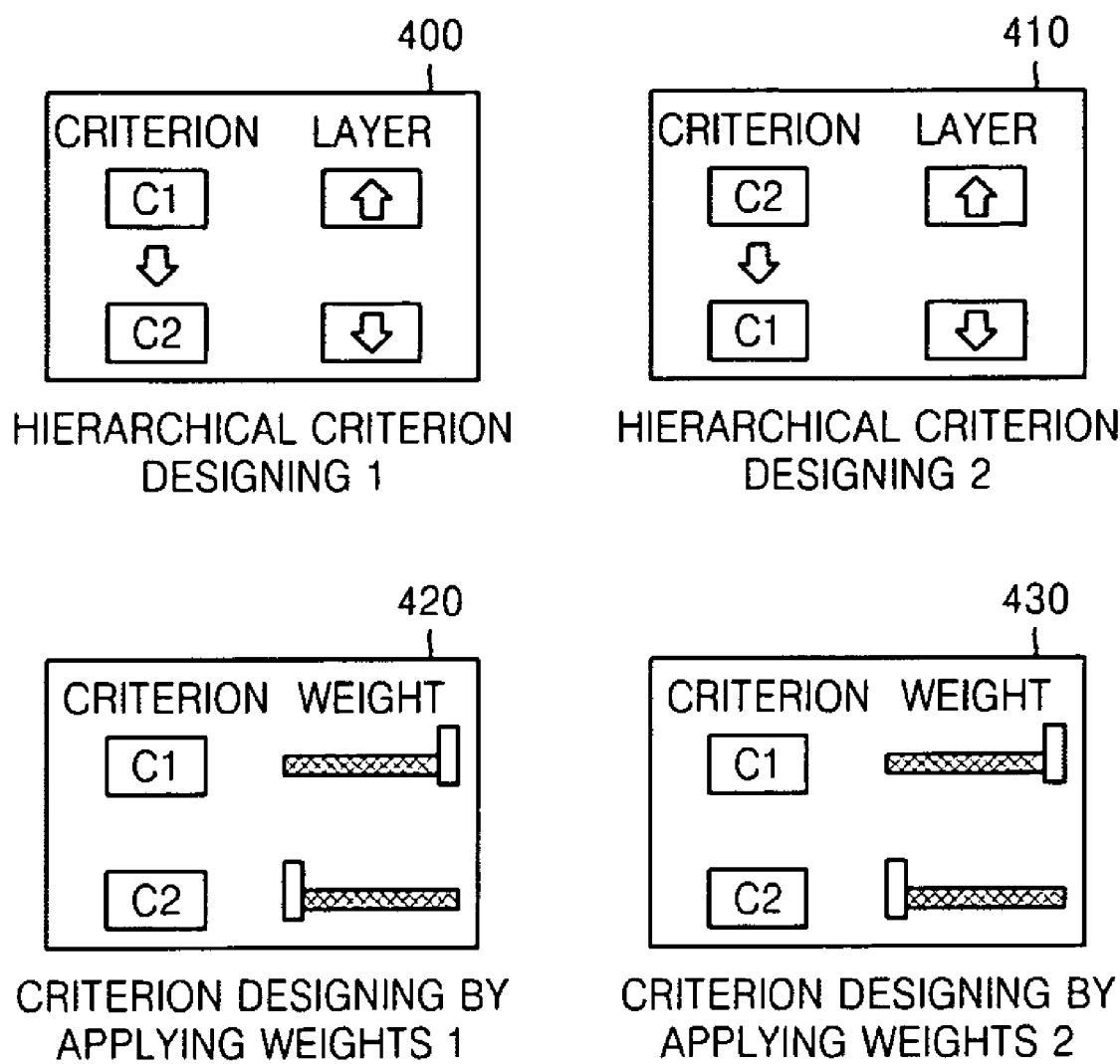
FIG. 4 illustrates designing of clustering criteria according to an exemplary embodiment of the present invention.

In criterion designing by applying weights, a weight of 0.3 and a weight of 0.7 may be applied to the "the number of 2D structures" clustering criterion and the "3D edge histogram" clustering criterion, respectively (see FIG. 4). When retrieval according to the "active site" clustering criterion is desired, clustering may be performed after the "active site" clustering criterion is added.

The input data processing unit 130 extracts characteristics from input data according to clustering criteria designed by the clustering criterion designing unit 120 and stores the extracted characteristics in the clustering characteristic database 140 in operation S220. In other words, various information to be used for clustering is extracted.

For example, when characteristics for protein structure-based clustering are extracted according to the "the number of 2D structures" clustering criterion, coordinates of an atom of each protein are received as input data and it is determined whether a 2D structure is an α-Helix or a β-Helix with reference to a distance between coordinates of the atom and cohesion in order to obtain the number of 2D structures. In other words, Table 1 is obtained as below.

TABLE 1

| Name of Protein | α-Helix | β-Helix |
|---|---|---|
| Protein-1 | 10 | 5 |
| Protein-2 | 5 | 2 |
| ... | ... | ... |
| Protein-N | 4 | 3 |

When the "sequence of 2D structures" clustering criterion is used, a characteristic of the sequence of 2D structures formed in a direction from an N terminal to a C terminal is extracted. For comparison between the extracted characteristics, string matching similarity process, which is generally used in sequence analysis, is used.

When the "3D edge histogram" clustering criterion is used, a characteristic of a local distribution pattern of bonds of atoms forming a backbone of protein is extracted.

When the "regression" clustering criterion is used, the entire area of a protein structure is divided into 64 sub areas and a regression graph included in each of the sub areas serves as an extracted characteristic.

When the "Ramachandran map" clustering criterion is used, a characteristic of the number of $\phi$ and X that are present in each area of the Ramachandran map is extracted.

The clustering unit 150 performs clustering of the characteristics extracted by the input data processing unit 130. The clustering unit 150 first selects a clustering method for clustering in operation S230. The clustering method may be selected from various conventional methods. For example, there are distance-based clustering methods such as a K-means algorithm, an iterative self organizing data technique (ISODATA), a self organizing map (SOM), and a hierarchical clustering algorithm. Various initial values and factors for clustering may be set during an initializing process.

The clustering unit 150 performs clustering according to the selected clustering method in operation S240. If the result of clustering is acceptable in operation S250, the clustering unit 150 outputs the result of clustering through an output device (not shown) in operation S260.

For example, in a protein structure-based clustering system, the result of clustering takes the form of tree in the case of hierarchical criterion designing and includes only a first child node from the root of a clustering layered tree in the case of criterion designing by applying weights. By selecting each node from the clustering layered tree, samples of a cluster included in the node can be seen.

Meanwhile, the method of extracting and clustering information according to the present invention can also be embodied as a computer-readable code on a computer-readable recording medium. The computer-readable recording medium is any data storage device that can store data which can be thereafter read by a computer system. Examples of computer-readable recording media include read-only memory (ROM), random-access memory (RAM), CD-ROMs, magnetic tapes, floppy disks, and optical data storage devices. The computer-readable recording medium can also be distributed over network of coupled computer systems so that the computer-readable code is stored and executed in a decentralized fashion.

As described above, according to the present invention, the user can efficiently use a clustering system by reconstructing at least one criteria that are previously defined in the clustering system.

While the present invention has been particularly shown and described with reference to an exemplary embodiment thereof, it will be understood by those of ordinary skill in the art that various changes in form and detail may be made therein without departing from the spirit and scope of the present invention as defined by the following claims.

What is claimed is:

1. A system for extracting and clustering information, the system comprising:
   a clustering criterion designing unit reconstructing a hierarchy of a plurality of clustering criteria in order to design a new clustering criterion, at least one of the plurality of clustering criteria being defined by a user;
   an input data processing unit extracting characteristics from input data based on the new clustering criterion; and
   a clustering unit performing clustering of the extracted characteristics using the hierarchy of the plurality of clustering criteria, in which the extracted characteristics are clustered by a first criterion of the plurality of criteria to produce a result and the result is further clustered by a second criterion of the plurality of criteria,
   wherein the clustering unit performs clustering on the characteristics based on a clustering method selected from the group consisting of a K-means algorithm, an iterative self organizing data technique (ISODATA), a self organizing map (SOM), and a hierarchical clustering algorithm, said clustering unit outputting to an output device the results of said clustering.

2. The system of claim 1, further comprising a clustering criterion database storing the plurality of clustering criteria.

3. The system of claim 2, further comprising a clustering criterion storing/deleting unit adding an additional clustering criterion defined by the user to the clustering criterion database or deleting a clustering criterion stored in the clustering criterion database at the user's request.

4. The system of claim 1, further comprising a clustering characteristics database storing the characteristics extracted by the input data processing unit, wherein the clustering unit performs clustering on the characteristics stored in clustering characteristics database.

5. The system of claim 1, wherein the plurality of clustering criteria include clustering criteria for a protein structure, including the number of two-dimensional (2D) structures, the distribution of 2D structures, the sequence of the 2D structures, a protein sequence, a three-dimensional (3D) edge histogram, regression, and a Ramachandran map, and the input data is data of a protein 3D structure database.

6. The system of claim 1, wherein the clustering criterion designing unit applies weights to the plurality of clustering criteria to design the new clustering criterion.

7. The system of claim 1, wherein the at least one criterion defined by the user includes an active sites criterion to cause data to be clustered according to similarity of active sites.

8. A method of extracting and clustering information, the method comprising computer readable code stored on a computer readable storage medium, said computer readable code when executed by a processor:
   reconstructing a hierarchy of a plurality of clustering criteria in order to design a new clustering criterion, at least one of the plurality of clustering criteria being defined by a user;
   extracting characteristics from input data according to the new clustering criterion; and
   performing clustering of the extracted characteristics using the hierarchy of the plurality of clustering criteria, in which the extracted characteristics are clustered by a first criterion of the plurality of criteria to produce a result and the result is further clustered by a second criterion of the plurality of criteria,
   wherein the clustering is performed on the characteristics based on a clustering method selected from the group consisting of a K-means algorithm, an iterative self organizing data technique (ISODATA), a self organizing map (SOM), and a hierarchical clustering algorithm.

9. The method of claim 8, wherein the plurality of clustering criteria include clustering criteria for a protein structure, including the number of two-dimensional (2D) structures, the distribution of 2D structures, the sequence of the 2D structures, a protein sequence, a three-dimensional (3D) edge histogram, regression, and a Ramachandran map, and the input data is data of a protein 3D structure database.

10. The method of claim 8, further comprising:
    applying weights to the plurality of clustering criteria to design the new clustering criterion.

11. The method of claim 8, wherein the at least one criterion defined by the user includes an active sites criterion to cause data to be clustered according to similarity of active sites.

* * * * *